(12) United States Patent
Koskinen et al.

(10) Patent No.: US 7,727,543 B2
(45) Date of Patent: *Jun. 1, 2010

(54) BIODEGRADABLE CARRIER AND METHOD FOR PREPARATION THEREOF

(75) Inventors: Mika Koskinen, Turku (FI); Eija Säilynoja, Turku (FI); Manja Ahola, Piikkiö (FR); Harry Jalonen, Turku (FI); Jukka Salonen, Turku (FI); Veli-Matti Kähäri, Turku (FI)

(73) Assignee: DelSiTech Oy, Turku (FI)

( * ) Notice: Subject to any disclaimer, the term of this patent is extended or adjusted under 35 U.S.C. 154(b) by 0 days.

This patent is subject to a terminal disclaimer.

(21) Appl. No.: 12/343,030

(22) Filed: Dec. 23, 2008

(65) Prior Publication Data

US 2009/0104245 A1 Apr. 23, 2009

Related U.S. Application Data

(63) Continuation of application No. 10/473,774, filed as application No. PCT/FI02/00079 on Feb. 1, 2002, now Pat. No. 7,485,318.

(60) Provisional application No. 60/281,026, filed on Apr. 4, 2001.

(30) Foreign Application Priority Data

Apr. 4, 2001 (FI) .................... 20010698

(51) Int. Cl.
  *A61K 9/00* (2006.01)
  *A61K 39/00* (2006.01)
  *A61K 39/235* (2006.01)
  *A01N 63/00* (2006.01)
  *C12N 7/00* (2006.01)
  *C12N 7/01* (2006.01)

(52) U.S. Cl. ............... 424/426; 424/486; 424/204.1; 424/199.1; 424/233.1; 424/93.2; 424/93.6; 435/235.1

(58) Field of Classification Search .......... None
  See application file for complete search history.

(56) References Cited

U.S. PATENT DOCUMENTS

| | | | |
|---|---|---|---|
| 5,077,213 A | 12/1991 | Li et al. ............ 435/235.1 |
| 5,591,453 A | 1/1997 | Ducheyne et al. ........... 424/484 |
| 5,817,327 A | 10/1998 | Ducheyne et al. ........... 424/425 |
| 5,942,496 A * | 8/1999 | Bonadio et al. ............ 514/44 A |
| 6,410,011 B1 | 6/2002 | Branellec et al. .......... 424/93.2 |
| 6,425,918 B1 | 7/2002 | Shapiro et al. .......... 623/11.11 |
| 6,485,721 B1 | 11/2002 | Yoshida et al. .......... 424/93.21 |
| 6,632,648 B1 | 10/2003 | Kampinga et al. |
| 6,689,600 B1 | 2/2004 | Wu et al. |

FOREIGN PATENT DOCUMENTS

| EP | 0 679 402 | 11/1995 |
|---|---|---|
| JP | 62-228024 | 10/1987 |
| WO | WO 93/04196 | 3/1993 |
| WO | WO 97/45367 | 12/1997 |
| WO | WO 00/32233 * | 6/2000 |
| WO | WO 01/13924 | 3/2001 |
| WO | WO 01/15751 | 3/2001 |

OTHER PUBLICATIONS

Fennouh et al (Journal of Sol-Gel Science and Technology 19:647-649, 2000).*
Livage et al (Journal of Physics: Condensed Matter 13: R673-R691, 2001).*
Conroy et al (Journal of the Association for Laboratory Automation 5: 52-57, 2000).*
Beer et al., "Poly(lactic-glycolic) acid copolymer encapsulation of recombinant adenovirus reduces immunogenicity in vivo," 5 *Gene Therapy* 740 (1998).
Grill et al., "The Organotypic Multicellular Spheroid is a Relevant Three-Dimensional Model to Study Adenovirus Replication and Penetration in Human Tumors in Vitro," 6 *Molecular Therapy* 609 (2002).
Fields, Virology, Third Edition, vol. 1, Lippincott Williams, pp. 65, 101, 102 (1996).
Wu et al., "Production of Viral Vectors for Gene Therapy Applications," 11 *Current Opinions in Biotechnology* 205 (2000).
Peralta-Perez et al., "SiO$_2$ Xerogel: A Suitable Support for Microbial Growth," 20 *J. Sol-Gel Sci. & Tech.* 105 (2001).
*Donatti et al., "A Kinetic Study of Drying of Teos-Derived Gels Under Nearly Isothermal Conditions," 2 *Materials Res.* 43 (1999).

* cited by examiner

*Primary Examiner*—Mary E Mosher
(74) *Attorney, Agent, or Firm*—James C. Lydon

(57) ABSTRACT

A biodegradable carrier is produced for preservation and/or controlled delivery of biologically active agents where said biodegradable carrier is a silica xerogel which is made from water and silane by using acid or base as a catalyst, and biologically active agents in said biodegradable carrier are infecting and/or transfecting viruses. Silica xerogel material can be pharmaceutically acceptable and it can be used as a medicine.

7 Claims, No Drawings

BIODEGRADABLE CARRIER AND METHOD FOR PREPARATION THEREOF

This application is a continuation of Ser. No. 10/473,774 filed Oct. 03, 2003, now U.S. Pat. No. 7,485,318, which is a U.S. National Stage of International application PCT/F102/00079, filed Feb. 1, 2002, and which claims priority of U.S. provisional application No. 60/281,026, filed Apr. 4, 2001 and Finnish patent application No. 20010698, filed Apr. 4, 2001.

This invention concerns a biodegradable carrier and a method for preparation of said carrier for preservation and/or controlled delivery of biologically active agents.

BACKGROUND

The use of biodegradable materials for controlled delivery of biologically active agents has become more important in recent years. The biodegradable material can be e.g. silica sol-gel.

The sol-gel technology is based on hydrolyzation of metal-alkoxide (silane) and subsequent polymerization of metal hydroxides where three reaction steps can be identified. The three reaction steps are:

1. Hydrolysis

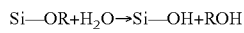
Si—OR+H$_2$O→Si—OH+ROH

2. Condensation of Alcohol

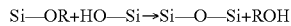
Si—OR+HO—Si→Si—O—Si+ROH

3. Condensation of Water

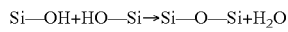
Si—OH+HO—Si→Si—O—Si+H$_2$O

These reactions can be modified by using different Si—OR reagents, for example tetraethoxysilane (TEOS) or tetramethoxysilane can be used. Also the silane-water ratio can be modified, and water can partly be replaced with a suitable alcohol (methanol in methoxygel and ethanol in ethoxygel). Different additives, such as polyethyleneglycol, may also be used to introduce novel properties into the material. In all cases, the reaction is carried out by using acid or base as catalyst. By using a catalyst, it is possible to prepare sol-gel without any resembling alcohol, for example ethanol addition is not necessary in gels prepared from TEOS.

Silica sol-gel technology is economical and easy to use. Silica products are usually biocompatible and non-toxic. It has been shown that chemical and physical changes of silica xerogel have an effect on the releasing behavior of biologically active agents embedded in the gel. The sol-gel technique thus offers versatile possibilities for incorporation and controlled delivery of biologically active agents. These biologically active molecules can according to prior art (WO 9745367, Ahola et al, 1997; FI 19991806, Ahola et al 1999) be for example proteins (growth factors), hormones, nucleic acids (RNA, DNA) or polysaccharides. Also parts from virus capsids or whole viruses can be used, particularly for vaccination. Toremifene citrate, Selegiline hydrochloride, (−)-4-(5-fluoro-2,3-dihydro-1H-inden-2-yl)-1H-imidazole hydrochloride, ibuprofen, caffeine, peptides (levodopa), proteins (a dental enamel matrix derivative) and heparin have been used.

Silica xerogel has been made e.g. by using water, alkoxide and methanol at a temperature of 0° C. by adjusting the pH to a value between 1 and 4.5, preferably to a value between about 1.5 and 3.0, adding a biologically active molecule and allowing the mixture to gel and age at temperatures from about 0° C. up to about +40° C. and then drying the aged gel at temperatures from about +15° C. up to about +40° C. (U.S. Pat. No. 5,817,327, Ducheneye et al. 1998).

A method has been described where active molecules are entrapped in a porous, transparent glass, which has been formed using sol-gel process. The aim of this process was to make transparent glasses that are not biologically degradable so that the reactions of biologically active materials occur inside the gel and nothing is released. For this purpose a metal alkoxide is mixed with water resembling alcohol and exposed to ultrasonic energy. The single-phase solution is then mixed with an active biological material and the resultant gel is aged and dried. The active biological material is then trapped in a monolith of the gel. (WO 9304196)

In gene therapy, genes are usually administered to patients by using injections. Possible gene transfer vectors are plasmids, naked DNA or viral vectors, such as adenoviruses, adeno associated virus or retroviruses. In some application, it may be advantageous also to have a carrier, so that targeting into the desired tissue can take place without the need to use an excess of vector and/or prolong the local effect of the vector.

OBJECTS AND SUMMARY OF THE INVENTION

The aim of this invention is to provide a method that makes it possible to add viruses as biologically active agents into a biodegradable gel so that viruses do not loose their activity to infect and/or transfect cells. Thus, it is possible to prepare material to be used for preservation and/or controlled delivery of biologically active agents, like viruses.

In this method biodegradable silica xerogel carrier containing viruses as biologically active agent is made using an acid or a base as catalyst. The solution of water and silane is homogenized by stirring. After the homogeneity of the solution is reached, the pH of this solution is adjusted to a value suitable for added viruses, e.g. which is preferably from 4.9 to 7.0. The solution is not allowed to gel and the viruses are added into this solution while stirring. Then the stirring of the solution is stopped and the solution is allowed to gel.

Gelification is preferably made inside a gelification chamber holding a mould for gel. The solution is preferably allowed to gel in conditions allowing evaporation of reaction products released during said gelification. The mould is preferably left open to allow maximal evaporation of reaction products, e.g. ethanol and water. Drying can preferably be made in vacuum and/or at the presence of drying agents, e.g. siccative or CaCl$_2$.

This silica xerogel material can be pharmacologically acceptable so that it can be used in pharmaceutical preparations as e.g. monoliths, cones, fibers, webs or multiparticles (particle size e.g. 1 nm-100 µm), or as coating material for different types of implants, such as urethral and vascular stents. Implants may also be made antibacterial by coating them with gel containing certain bacteriophages.

DETAILED DESCRIPTION

The term "biological active agent" shall be understood as an agent causing a desired effect in vivo, ex vivo or in vitro.

The term "infectivity" shall be understood as internalization of a virus into the cell by a cell mediated process.

The term "transfectivity" shall be understood as the biological process where the genome of an infecting virus is expressed inside a cell.

The term "controlled delivery" shall be understood as controlled release of delivered agents at a desired target and/or at a desired moment and/or time period.

The term "silica xerogel" shall be understood as solid silica material or partly wet silica material where the main part of said material is solid.

It is novel and inventive to have viruses, e.g. adenoviruses, adeno associated viruses, retroviruses or bacteriophages, as biologically active agents in biodegradable gel so that they maintain their activity to infect and/or transfect cells for a prolonged period of time.

In this new method a biodegradable silica xerogel carrier is made from water and silane by using an acid or a base as catalyst at temperatures below +15° C., preferably at temperatures 0° C. to +10° C. Different metal-alkoxides (silanes) can be used to modify these reactions, for example tetraethoxysilane (TEOS) or tetramethoxysilane can be used. Also the water silane ratio can be altered, the molar ratio can e.g. be 10-60 when using TEOS as silane. An optimal molar water silane ratio can also be e.g. 35-50, 45-60 or 50-75 depending on the used silane and added viruses.

The solution is first homogenized with constant stirring. After the homogeneity of the solution is reached, its pH is adjusted to a value suitable for added viruses, e.g. preferably from 4.9 to 7.0 or preferably to a value from 6.0 to 7.0. The solution is not allowed to gel and viruses are added into this solution. The stirring of the solution is then stopped and the solution is allowed to gel. The solution is preferably allowed to gel at the temperature of below +15° C., preferably at temperatures 0° C. to +10° C. For neutralizing the solution ammonium hydroxide, sodium hydroxide for acid catalyzed process or hydrochloride acid acetic acid for base catalyzed process can be used. Also other bases or acids may be used.

Gelification is preferably made inside a gelification chamber, which allows the control of the temperature and humidity. Inside this chamber evaporation of reaction products, e.g. ethanol and water, can take place at normal or preferably at reduced pressure in vacuum. Also drying material can be present in the gelification chamber.

By using this new method a preservation and/or controlled delivery system can be designed even for viruses that loose their activity very rapidly in conventional solutions. For example adenoviruses are known to rapidly loose their infecting and transfecting ability in the absence of cell contact. According to this invention viruses added to this solution can maintain their transfecting ability for at least 18 days in a silica xerogel material produced. This demonstrates the stabilizing and preserving effect of the xerogel.

The described method is essentially better compared to methods that are currently used. Viruses can keep their infecting and/or transfecting activity in silica xerogel made by this new method even several weeks at about +37° C. Free viruses usually loose their transfectivity in shorter time periods unless they are kept frozen.

Water can be partly supplemented with a suitable alcohol (ethanol in ethoxygel, for example). Different additives, such as polyethyleneglycol, may be used to introduce novel properties into the material. The acid catalyst can be e.g. acetic acid or hydrochloric acid. Also other organic and inorganic acids can be used. In a base catalyzed process ammonium hydroxide or sodium hydroxide can be used. Also other weak or strong bases can be used.

According to the invention, the said viruses, e.g. adenoviruses, adeno associated viruses, retroviruses, are capable of infecting and/or transfecting target cells. The genetic material thus released allows its replication and expression of possible transgene in the target cell.

The material can be used as a medicine and it can be used for the manufacture of a medicine. This material can be used for neurological, oncological and tissue repair applications. These applications include for example cardiovascular therapy, diabetes therapy, arteritis therapy, wound repair, bone lesion repair and treatment of osteoporosis. Thus, the material can be used to treat neurological, oncological and/or tissue illness.

One application is to embed bacteriophages in silica xerogel and then coat an implant with it and thus achieve an antibacterial coating.

The silica xerogel can bear more than one biologically active agent. It can be designed to a multilayered coating or block of material, where each layer carries different properties. The silica xerogel can also be a core material. Thus, the biologically active agents can be incorporated in the core material and/or a preferred coating layer or any preferred layers. The different biologically active agents can be incorporated in the same or different layers or in the core material. Further the biologically active agent can be designed to be incorporated in a desired region of the core or any layer of the material block.

The silica xerogel material can be added to a device to be implanted into the human or animal body to serve different clinical goals described, e.g. for biologically active stents, implants (dental or orthopedic), implants for controlled drug delivery, etc. The viruses must then be pharmacologically and medically acceptable in vivo and ex vivo.

EXPERIMENTAL

Brief Introduction

The basic aim was to prepare silica gels suitable for incorporating adenoviruses and to evaluate whether said adenoviruses maintain their ability to transfect eucaryotic cells after the procedure. The investigation was carried out in vitro using a cell line that is easily transfected by adenoviruses and a replication deficient recombinant, easily detectable lacZ gene carrying adenovirus.

Materials & Methods

Silica Xerogel

Silica xerogel was prepared aseptically with sterilized deionized water and sterile equipment. The reaction for preparing the silica gel was carried out in an ice/water bath (0° C.) with constant and vigorous stirring. The system consisted of 5 ml of sterile, deionized water and 1.2 ml of TEOS (tetraethoxysilan, Aldrich). The molar ratio of water and TEOS was 48:1. The reaction was catalyzed with 50 µl of acetic acid (99 to 100%, Baker). Hydrolysis was continued in an ice/water bath with vigorous stirring until homogeneity was reached. Homogeneity was detected visually (a clear solution was regarded homogenous). After this reaction step the pH of the solution was adjusted to 6.6 by using 1 M $NH_4OH$ (ammonium hydroxide, Merck). This step was done very carefully since after having reached the turning point, gelification takes place very rapidly. The average amount of $NH_4OH$ solution needed was 1.9 ml. Viruses were added into this solution while vigorously stirring the solution. Final virus content of the solution was about $4.14 \cdot 10^7$ pfu/ml. The stirring of the solution was stopped and 400 µl aliquots were taken from the solution prepared into a 24-well plate (400 µl into each well) and the plate was left open and put into a sterile desiccator (=gelification chamber) with siccative inside. Then the plate was transferred into a refrigerator (+4° C.) and the gelification was allowed to take place. Siccative was changed reasonable often so that humidity balance between virus-gel and siccative was avoided.

Viruses

Viruses used were replication deficient recombinant adenoviruses carrying lacZ-gene, RadLacZ (Wilkinson, G. W. G., Akrigg, A., Nucleic Acids Research 1992: 20: 2233-2239).

Cell Cultures

Cell line used was HT1080 (Raisheed S., et al. Cancer 1974: 33(4): 1027-1033. This cell line is very easily infected by adenoviruses (Ala-aho, R. et al., Int. J. Cancer 2002: 97:283-289). The cells were cultured in normal cell culture conditions (+37° C., 5% $CO_2$ in humidified atmosphere). Cell culture medium was DMEM (Dulbecco's Modified Eagle's Medium, Sigma) with 10% iFCS (inactivated Foetal Calf Serum, Haemek, Kibbutz Beit Israel), 20 mM HEPES (Sigma), penicillin-streptomycin (GibcoBRL) and fungizone (GibcoBRL). The cells were grown in 250 ml cell culture bottles and harvested at confluency. Medium was changed every other day.

For testing the release of viruses from gel buttons prepared as described above, two separate systems were created. In the first system the mould with xerogel monolith buttons was transferred after 9 days in +4° C. into a cell culture incubator. The HT1080 cells were cultured for 48 h on buttons that had been kept in the incubator for different periods of time (1, 3, 5, 9 days). After culture, the cells were stained with X-gal (Ahonen, M., et al., Cancer Res. 1998: 58:2310-2315), which stains transfected cells blue. As a control, the plain silica-gel with viruses and silica-gel without viruses but with cells were also stained. In the second system silica-gel buttons were transferred into sterile bottles containing 5 ml of cell culture medium. Constant number of HT1080 cells were added and cultured as suspensions. After 48 h culture period the cells and the medium were removed and replaced with fresh ones. The removed cells were cultured on cell culture dishes and stained with X-gal. The number of transfected cells was recorded.

About X-Gal Staining

The transfected cells expressed a β-galactosidase enzyme coded by the viral lacZ-gene. This enzyme is capable of using X-gal as substrate so that a blue colored product is produced. Transfected cells can then be detected.

X-Gal Staining

Virus transfection was detected using X-gal staining. First the medium was removed and then the cells were washed twice with PBS (phosphate buffered saline). Washed cells were fixed with formaline (0.4% formaldehyde+0.2% glutaraldehyde) for 5 minutes and washed again three times with PBS. Then the cell layer was covered with filtrated (0.22 μm pore size filter) X-gal solution (8.0 mg $K_3Fe(CN)_6$+10 mg $K_4Fe(CN)_6$+10 μl 1 M $MgCl_2$+200 μl 2% X-gal+4790 μl PBS) and incubated in cell culture conditions over night. Blue color indicated virus transfection.

Results

The cells on xerogel monolith buttons from the first system stained strongly with no difference between different time points (1, 3, 5, 9 days). A part of the stain was released from the cells into the xerogel. Controls remained unstained. This result demonstrates the virus preserving effect of the silica xerogel. The second system differs mainly from the first by the fact that xerogel buttons were in a liquid environment. The last time point in this experiment was 7 days (1, 3, 5, 7 days). The number of transfected cells increased toward the 5:th day of test being strong at this point. After 7 days the transfection was as strong as at the 5 days time point.

These experiments show that adenoviruses survived the gel manufacturing process. Further, it can be concluded that viruses survived the extended test period, which was 18 days in former and 7 days in latter experiment, thus demonstrating the virus preserving property of the silica xerogel.

The invention claimed is:

1. A biodegradable composition for preservation or controlled delivery of at least one biologically active agent, said composition comprising a biodegradable carrier and a biologically active agent embedded in the carrier,
    wherein said biodegradable carrier is a silica xerogel which is made from water and silane by using an acid or a base as a catalyst,
    wherein said biologically active agent comprises an infective and/or transfective virus, and
    wherein a pH of a silica solution from which said silica xerogel is prepared is adjusted to 6.0 to 7.0 prior to addition of said virus.

2. The biodegradable composition of claim 1, wherein the silica xerogel is pharmaceutically acceptable.

3. The biodegradable composition of claim 1, wherein the biodegradable carrier is in the form of monoliths, fibers, nets, cones, multiparticles or a coating suitable for an implant material.

4. The biodegradable composition of claim 1, wherein said infective and/or transfective virus comprises a genetically modified virus.

5. The biodegradable composition of claim 1, wherein said virus is an adenovirus.

6. The biodegradable composition of claim 1, wherein said silane is tetraethoxysilane.

7. A method for the preparation of an implant suitable for virus therapy of neurological, oncological and tissue repair applications, comprising coating at least a portion of said implant with the biodegradable composition of claim 1.

* * * * *